US008162988B2

(12) United States Patent
Delecrin et al.

(10) Patent No.: US 8,162,988 B2
(45) Date of Patent: *Apr. 24, 2012

(54) PLATE FOR OSTEOSYNTHESIS DEVICE AND METHOD OF PREASSEMBLING SUCH DEVICE

(75) Inventors: Joël Delecrin, Vertou (FR); Jérôme Allain, Paris (FR); Patrick Tropiano, Marseilles (FR); Serge Ganglof, Aplerin (FR); Rémi Poncer, Vannes (FR)

(73) Assignee: LDR Medical, Rosières Près Troyes (FR)

( * ) Notice: Subject to any disclaimer, the term of this patent is extended or adjusted under 35 U.S.C. 154(b) by 427 days.

This patent is subject to a terminal disclaimer.

(21) Appl. No.: 10/492,827

(22) PCT Filed: Oct. 18, 2002

(86) PCT No.: PCT/IB02/04307

§ 371 (c)(1),
(2), (4) Date: Jul. 15, 2004

(87) PCT Pub. No.: WO03/032851

PCT Pub. Date: Apr. 24, 2003

(65) Prior Publication Data

US 2005/0010215 A1 Jan. 13, 2005

(30) Foreign Application Priority Data

Oct. 18, 2001 (FR) .................................... 01 13460

(51) Int. Cl.
*A61B 17/70* (2006.01)
(52) U.S. Cl. ..................................................... 606/266
(58) Field of Classification Search ................ 606/61, 606/69–73
See application file for complete search history.

(56) References Cited

U.S. PATENT DOCUMENTS 1,022,999 A 4/1912 Bashaw
(Continued)

FOREIGN PATENT DOCUMENTS

CA 1304267 6/1992
(Continued)

OTHER PUBLICATIONS

A unique self-contained connexion; Website: www.ldrmedical.dr/connexion_uk.htm; Oct. 11, 2004.
(Continued)

*Primary Examiner* — Eduardo C Robert
*Assistant Examiner* — David Comstock
(74) *Attorney, Agent, or Firm* — Denko Coburn & Lauff LLP (57) ABSTRACT

An osteosynthesis device is proposed, particularly for spinal support or correction, enabling easier and compact implantation, that can be particularly used in the case of implantation via the anterior approach, and a preassembly method for such a device. In various embodiments, the device comprises implants screwed into two vertebrae (0) and a plate (2) used to hold and displace the spine. In various embodiments, the plate (2) comprises on at least one of its ends at least one longitudinally elongated opening, the opening having firstly at least one part opening onto an edge of the plate, or one part of a sufficiently large size (s210b) to be able to be inserted without disassembly in the fixation means of an implant (1) already screwed into the spine when the fixation means are already assembled.

28 Claims, 8 Drawing Sheets

U.S. PATENT DOCUMENTS

| | | | |
|---|---|---|---|
| 1,191,676 A | 7/1916 | Di Maggio | |
| 1,750,687 A | 3/1930 | Pitkin | |
| 4,041,939 A | 8/1977 | Hall | |
| 4,047,524 A | 9/1977 | Hall | |
| 4,055,385 A | 10/1977 | Bjors | |
| 4,429,690 A * | 2/1984 | Angelino-Pievani | 606/69 |
| 4,648,388 A | 3/1987 | Steffee | |
| 4,653,481 A | 3/1987 | Howland et al. | |
| 4,696,290 A | 9/1987 | Steffee | |
| 4,773,402 A | 9/1988 | Asher et al. | |
| 4,946,458 A | 8/1990 | Harms et al. | |
| 5,007,880 A | 4/1991 | Walker | |
| 5,024,213 A | 6/1991 | Asher et al. | |
| 5,067,955 A | 11/1991 | Cotrel | |
| 5,092,893 A | 3/1992 | Smith | |
| 5,129,899 A | 7/1992 | Small et al. | |
| 5,176,680 A | 1/1993 | Vignaud et al. | |
| 5,197,986 A | 3/1993 | Mikhail | |
| 5,226,766 A | 7/1993 | Lasner | |
| 5,269,784 A | 12/1993 | Mast | |
| 5,275,600 A | 1/1994 | Allard et al. | |
| 5,282,863 A | 2/1994 | Burton | |
| 5,314,477 A | 5/1994 | Marnay | |
| 5,330,473 A | 7/1994 | Howland | |
| 5,344,421 A | 9/1994 | Crook et al. | |
| 5,358,526 A | 10/1994 | Tornier | |
| 5,374,267 A | 12/1994 | Siegal | |
| 5,401,269 A | 3/1995 | Buttner-Janz et al. | |
| 5,437,669 A | 8/1995 | Yuan et al. | |
| 5,456,698 A | 10/1995 | Byland et al. | |
| 5,486,174 A | 1/1996 | Fournet-Fayard et al. | |
| 5,486,176 A * | 1/1996 | Hildebrand et al. | 606/71 |
| 5,501,684 A | 3/1996 | Schlapfer | |
| 5,520,689 A | 5/1996 | Schlapfer et al. | |
| 5,531,747 A | 7/1996 | Ray | |
| 5,536,268 A | 7/1996 | Griss | |
| 5,545,163 A * | 8/1996 | Miller et al. | 606/61 |
| 5,545,167 A * | 8/1996 | Lin | 606/61 |
| 5,578,033 A | 11/1996 | Errico et al. | |
| 5,582,612 A * | 12/1996 | Lin | 606/61 |
| 5,584,833 A | 12/1996 | Fournet-Fayard et al. | |
| 5,584,834 A | 12/1996 | Errico et al. | |
| 5,591,166 A | 1/1997 | Bernhardt et al. | |
| 5,601,552 A | 2/1997 | Cotrel | |
| 5,603,714 A | 2/1997 | Kaneda et al. | |
| 5,609,592 A | 3/1997 | Brumfield et al. | |
| 5,613,968 A * | 3/1997 | Lin | 606/61 |
| 5,620,443 A * | 4/1997 | Gertzbein et al. | 606/61 |
| 5,628,740 A | 5/1997 | Mullane | |
| 5,651,789 A | 7/1997 | Cotrel | |
| 5,725,528 A | 3/1998 | Errico et al. | |
| 5,733,286 A | 3/1998 | Ralph et al. | |
| 5,735,851 A | 4/1998 | Errico et al. | |
| 5,738,586 A | 4/1998 | Arriaga | |
| 5,743,907 A | 4/1998 | Asher et al. | |
| 5,743,911 A | 4/1998 | Cotrel | |
| RE35,784 E | 5/1998 | Linkow et al. | |
| 5,782,833 A | 7/1998 | Haider | |
| 5,797,911 A | 8/1998 | Sherman et al. | |
| 5,800,435 A | 9/1998 | Errico et al. | |
| 5,833,418 A | 11/1998 | Shoji | |
| 5,876,403 A | 3/1999 | Shitoto | |
| 5,899,903 A | 5/1999 | Cotrel | |
| 5,910,142 A | 6/1999 | Tatar | |
| 5,938,663 A | 8/1999 | Petreto | |
| 5,947,965 A * | 9/1999 | Bryan | 606/61 |
| 5,947,966 A | 9/1999 | Drewry et al. | |
| 5,951,557 A * | 9/1999 | Luter | 606/286 |
| 5,984,928 A | 11/1999 | Hermann | |
| 5,989,250 A | 11/1999 | Wagner et al. | |
| 5,989,254 A | 11/1999 | Katz | |
| 6,030,389 A | 2/2000 | Wagner et al. | |
| 6,045,552 A | 4/2000 | Zucherman et al. | |
| 6,050,997 A | 4/2000 | Mullane et al. | |
| 6,053,921 A | 4/2000 | Wagner et al. | |
| 6,063,090 A | 5/2000 | Schlapfer | |
| 6,063,121 A | 5/2000 | Xavier et al. | |
| 6,066,140 A | 5/2000 | Gertzbein et al. | |
| 6,074,393 A | 6/2000 | Sitoto | |
| 6,077,262 A | 6/2000 | Schlapfer et al. | |
| 6,083,224 A | 7/2000 | Gertzbein et al. | |
| 6,113,601 A | 9/2000 | Tatar | |
| 6,117,135 A | 9/2000 | Schlapfer | |
| 6,123,706 A | 9/2000 | Lange | |
| 6,129,730 A * | 10/2000 | Bono et al. | 606/73 |
| 6,132,430 A | 10/2000 | Wagner | |
| 6,136,000 A * | 10/2000 | Louis et al. | 606/61 |
| 6,136,002 A * | 10/2000 | Shih et al. | 606/61 |
| 6,206,879 B1 * | 3/2001 | Marnay et al. | 606/53 |
| 6,214,012 B1 * | 4/2001 | Karpman et al. | 606/93 |
| RE37,161 E | 5/2001 | Michelson et al. | |
| 6,235,034 B1 | 5/2001 | Bray | |
| 6,248,104 B1 | 6/2001 | Chopin et al. | |
| 6,248,105 B1 | 6/2001 | Schlapfer et al. | |
| 6,254,603 B1 | 7/2001 | Gertzbein et al. | |
| 6,261,288 B1 | 7/2001 | Jackson | |
| 6,264,658 B1 | 7/2001 | Lee et al. | |
| 6,277,119 B1 | 8/2001 | Walulik et al. | |
| 6,280,445 B1 * | 8/2001 | Morrison et al. | 606/61 |
| 6,287,309 B1 * | 9/2001 | Baccelli et al. | 606/61 |
| 6,306,136 B1 * | 10/2001 | Baccelli | 606/61 |
| 6,344,057 B1 | 2/2002 | Rabbe et al. | |
| 6,355,038 B1 * | 3/2002 | Pisharodi | 606/61 |
| 6,371,988 B1 | 4/2002 | Pafford et al. | |
| 6,391,030 B1 | 5/2002 | Wagner et al. | |
| 6,413,259 B1 | 7/2002 | Lyons et al. | |
| 6,416,515 B1 | 7/2002 | Wagner | |
| 6,454,769 B2 | 9/2002 | Wagner et al. | |
| 6,458,132 B2 | 10/2002 | Choi | |
| 6,471,704 B2 | 10/2002 | Gertzbein et al. | |
| 6,475,218 B2 | 11/2002 | Gournay et al. | |
| 6,478,798 B1 | 11/2002 | Howland | |
| 6,488,682 B2 | 12/2002 | Kikuchi et al. | |
| 6,506,216 B1 | 1/2003 | McCue et al. | |
| 6,547,790 B2 | 4/2003 | Harkey, III et al. | |
| 6,551,322 B1 | 4/2003 | Lieberman | |
| 6,554,831 B1 | 4/2003 | Rivard et al. | |
| 6,562,040 B1 | 5/2003 | Wagner | |
| 6,565,565 B1 | 5/2003 | Yuan et al. | |
| 6,565,605 B2 | 5/2003 | Goble et al. | |
| 6,579,319 B2 | 6/2003 | Goble et al. | |
| 6,585,738 B1 * | 7/2003 | Mangione et al. | 606/61 |
| 6,595,992 B1 | 7/2003 | Wagner et al. | |
| 6,602,254 B2 | 8/2003 | Gertzbein et al. | |
| 6,610,063 B2 | 8/2003 | Kumar et al. | |
| 6,613,050 B1 | 9/2003 | Wagner et al. | |
| 6,613,053 B1 * | 9/2003 | Collins et al. | 606/69 |
| 6,616,664 B2 | 9/2003 | Walulik et al. | |
| 6,620,164 B2 | 9/2003 | Ueyama et al. | |
| 6,641,583 B2 * | 11/2003 | Shluzas et al. | 606/61 |
| 6,641,585 B2 | 11/2003 | Sato et al. | |
| 6,641,586 B2 | 11/2003 | Varieur | |
| 6,663,631 B2 | 12/2003 | Kuntz | |
| 6,669,697 B1 | 12/2003 | Pisharodi | |
| 6,682,530 B2 * | 1/2004 | Dixon et al. | 606/61 |
| 6,682,533 B1 | 1/2004 | Dinsdale et al. | |
| 6,702,814 B2 | 3/2004 | Walulik et al. | |
| 6,702,815 B2 | 3/2004 | Kuntz | |
| 6,726,687 B2 | 4/2004 | Jackson | |
| 6,736,816 B2 | 5/2004 | Ritland | |
| 6,749,613 B1 * | 6/2004 | Conchy et al. | 606/61 |
| 6,755,829 B1 | 6/2004 | Bono et al. | |
| 6,884,241 B2 * | 4/2005 | Bertranou et al. | 606/61 |
| 6,994,727 B2 | 2/2006 | Khandkar et al. | |
| 7,060,097 B2 | 6/2006 | Fraser et al. | |
| 7,204,852 B2 | 4/2007 | Marnay et al. | |
| 2001/0001119 A1 | 5/2001 | Lombardo | |
| 2001/0010000 A1 | 7/2001 | Gertzbein et al. | |
| 2001/0047173 A1 | 11/2001 | Schlaepfer et al. | |
| 2002/0010467 A1 | 1/2002 | Cooper et al. | |
| 2002/0013585 A1 | 1/2002 | Gournay et al. | |
| 2002/0193795 A1 | 12/2002 | Gertzbein et al. | |
| 2003/0045875 A1 | 3/2003 | Bertranou et al. | |
| 2003/0088251 A1 | 5/2003 | Braun et al. | |
| 2003/0114853 A1 | 6/2003 | Burgess et al. | |
| 2003/0187441 A1 | 10/2003 | Bolger et al. | |
| 2004/0117022 A1 | 6/2004 | Marnay et al. | |

| | | | |
|---|---|---|---|
| 2004/0158251 A1 | 8/2004 | Morrison et al. | |
| 2004/0172020 A1 | 9/2004 | Beaurain et al. | |
| 2004/0243238 A1 | 12/2004 | Arnin et al. | |
| 2004/0254577 A1 | 12/2004 | Delecrin et al. | |
| 2005/0010215 A1 | 1/2005 | Delecrin et al. | |
| 2005/0027359 A1 | 2/2005 | Mashburn | |
| 2005/0060034 A1 | 3/2005 | Berry et al. | |
| 2005/0085917 A1 | 4/2005 | Marnay et al. | |
| 2005/0107788 A1 | 5/2005 | Beaurain et al. | |
| 2005/0131542 A1 | 6/2005 | Benzel et al. | |
| 2005/0149189 A1 | 7/2005 | Mokhtar et al. | |
| 2005/0197706 A1 | 9/2005 | Hovorka et al. | |
| 2006/0064091 A1 | 3/2006 | Ludwig et al. | |
| 2006/0069437 A1 | 3/2006 | Weber | |
| 2006/0149273 A1 | 7/2006 | Ross et al. | |
| 2006/0235526 A1 | 10/2006 | Lemaire | |
| 2007/0083201 A1 | 4/2007 | Jones et al. | |

FOREIGN PATENT DOCUMENTS

| | | |
|---|---|---|
| CA | 2443215 | 10/2002 |
| DE | 42 01 043 | 7/1993 |
| DE | 4201043 A | 7/1993 |
| DE | 19512709 A | 10/1996 |
| DE | 19545612 A | 6/1997 |
| DE | 19605640 A | 8/1997 |
| EP | 0274713 A | 7/1988 |
| EP | 0301489 A | 2/1989 |
| EP | 0490812 A | 6/1992 |
| EP | 0572790 A | 12/1993 |
| EP | 0679369 A | 11/1995 |
| EP | 0813845 A | 12/1997 |
| EP | 0846444 | 6/1998 |
| EP | 1250898 A | 10/2002 |
| EP | 1254640 A | 11/2002 |
| FR | 2659226 A | 9/1991 |
| FR | 2683445 | 5/1993 |
| FR | 2697993 | 5/1994 |
| FR | 2702361 A | 9/1994 |
| FR | 2704136 | 10/1994 |
| FR | 2 706 763 | 12/1994 |
| FR | 2706763 A | 12/1994 |
| FR | 2724108 A | 3/1996 |
| FR | 2 726 171 | 5/1996 |
| FR | 2726171 A | 5/1996 |
| FR | 2732887 A | 10/1996 |
| FR | 2735011 | 12/1996 |
| FR | 2765093 A | 12/1998 |
| FR | 2771918 A | 6/1999 |
| FR | 2823095 | 4/2001 |
| FR | 2827150 A | 1/2003 |
| FR | 2831048 | 4/2003 |
| FR | 2831049 | 4/2003 |
| FR | 2833151 | 6/2003 |
| FR | 2859095 | 3/2005 |
| FR | 2861981 A | 5/2005 |
| GB | 2178323 A | 2/1987 |
| JP | 09 098983 | 4/1997 |
| JP | 09098983 A | 4/1997 |
| WO | WO9307823 | 4/1993 |
| WO | WO9510240 A | 4/1995 |
| WO | WO9900065 | 1/1999 |
| WO | WO 99 33405 | 7/1999 |
| WO | WO9933405 A | 7/1999 |
| WO | WO9956675 A | 11/1999 |
| WO | WO0015125 A | 3/2000 |
| WO | WO 00 18312 | 4/2000 |
| WO | WO0018312 A | 4/2000 |
| WO | WO 01 01874 | 1/2001 |
| WO | WO0101874 A | 1/2001 |
| WO | WO0103592 A | 1/2001 |
| WO | WO0126566 A | 4/2001 |
| WO | WO 02 28299 | 4/2002 |
| WO | WO0228299 A | 4/2002 |
| WO | WO0230307 A | 4/2002 |
| WO | WO02080788 | 10/2002 |
| WO | WO03032850 A1 | 4/2003 |
| WO | WO03032851 | 4/2003 |
| WO | WO03039400 A2 | 5/2003 |
| WO | WO03049629 A1 | 6/2003 |
| WO | WO2004084742 | 10/2004 |
| WO | WO2005020829 A1 | 3/2005 |
| WO | WO2005044119 A2 | 5/2005 |

OTHER PUBLICATIONS

FR 2 704 136 Preliminary Search Report, National Institute of Industrial Property (France), Nov. 24, 1993.
FR 2 823 095 Preliminary Search Report, National Institute of Industrial Property (France), Dec. 20, 2001.
FR 2 827 150 Preliminary Search Report, National Institute of Industrial Property (France), Apr. 8, 2002.
FR 2 831 048 Preliminary Search Report, National Institute of Industrial Property (France), Jul. 3, 2002.
FR 2 831 049 Preliminary Search Report, National Institute of Industrial Property (France), Jul. 3, 2002.
FR 2 831 796 Preliminary Search Report, National Institute of Industrial Property (France), Aug. 2, 2002.
FR 2 833 151 Preliminary Search Report, National Institute of Industrial Property (France), Aug. 28, 2002.
FR 2 859 095 Preliminary Search Report, National Institute of Industrial Property (France), Apr. 14, 2004.
PCT/FR98/01363 (Publication WO9900065 Jan. 7, 1999), International Search Report, EPO, Oct. 14, 1998.
PCT/IB02/02827 International Search Report, EPO, Oct. 4, 2002.
PCT/IB02/04306 International Search Report, EPO, Feb. 4, 2003.
PCT/IB02/04307 International Search Report, EPO, Feb. 4, 2003.
PCT/IB02/04642 International Search Report, EPO, Jul. 2, 2003.
PCT/IB02/05302 International Search Report, EPO, Mar. 25, 2003.
PCT/IB04/002825 International Search Report, EPO, Jan. 7, 2005.
PCT/IB02/02827 International Preliminary Examination Report, EPO, May 15, 2003.
PCT/IB02/04306 International Preliminary Examination Report, EPO, Jul. 9, 2003.
PCT/IB02/04307 International Preliminary Examination Report, EPO, Jan. 13, 2004.
PCT/IB02/04642, International Preliminary Examination Report, EPO, Apr. 1, 2004.
PCT/IB02/05302 International Preliminary Examination Report, EPO, Mar. 23, 2004.
PCT/IB04/002825, International Preliminary Report on Patentability, EPO, Oct. 25, 2005.
PCT/IB04/002825, Written Opinion of the International Searching Authority, EPO, Jan. 5, 2005.
Product Bulletin, Acromed Corporation, Date Unknown.
Spinal Instrumentation, An and Cotler, 1992, Williams & Wilkins, pp. 399-400.
Spinal Product Systems, Zimmer, Date Unknown.
Stafix Plate System;Daruma, Date Unknown.
The Syracuse I-Plate, James C. Bayley, Md., et al., Department of Orthopedic Surgery, SUNY-HSC at Syracuse, Spine, vol. 16, No. 3 Supplement, Date Unknown.
TSRH Spinal Implant System, Danek Medical Inc., Date Unknown.
Un nouveau standard: la barre á méplat LDR; Website: www.ldrmedical.fr/easyspine.htm; Sep. 19, 2004.
PCT/IB08/001815, International Search Report and Written Opinion, EPO, Apr. 6, 2009.
USPTO OA of May 8, 2006 in U.S. Appl. No. 10/498,234.
USPTO OA of Dec. 26, 2006 in U.S. Appl. No. 10/498,234.
USPTO OA of Aug. 29, 2007 in U.S. Appl. No. 10/498,234.
USPTO OA of Nov. 21, 2007 in U.S. Appl. No. 10/498,234.
USPTO OA of Aug. 20, 2008 in U.S. Appl. No. 10/498,234.
USPTO OA of Sep. 12, 2005 in U.S. Appl. No. 10/473,999.
USPTO OA of May 4, 2006, in U.S. Appl. No. 10/473,999.
USPTO OA of Oct. 19, 2006 in U.S. Appl. No. 10/473,999.
USPTO OA of Jul. 30, 2007 in U.S. Appl. No. 10/473,999.
USPTO OA of Jan. 24, 2008 in U.S. Appl. No. 10/473,999.
UPSTO OA of Apr. 3, 2008 in U.S. Appl. No. 10/473,999.
USPTO OA of Jun. 14, 2006 in U.S. Appl. No. 10/492,753.
USPTO OA of Feb. 21, 2007, in U.S. Appl. No. 10/492,753.
USPTO OA of Oct. 16, 2007, in U.S. Appl. No. 10/492,753.
USPTO OA of Oct. 6, 2008, in U.S. Appl. No. 10/492,753.
Reply to USPTO OA of Nov. 21, 2007 in U.S. Appl. No. 10/498,234.

Reply to USPTO Action of May 8, 2006 in U.S. Appl. No. 10/498,234.
Reply to USPTO Action of Dec. 26, 2006 in U.S. Appl. No. 10/498,234.
Reply to USPTO Action of Aug. 29, 2007 in U.S. Appl. No. 10/498,234.
Reply to USPTO OA of Sep. 12, 2005 in U.S. Appl. No. 10/473,999.
Reply to USPTO OA of May 4, 2006, in U.S. Appl. No. 10/473,999.
Reply to USPTO OA of Oct. 19, 2006 in U.S. Appl. No. 10/473,999.
Reply to USPTO OA of Jul. 30, 2007 in U.S. Appl. No. 10/473,999.
Reply to USPTO OA of Apr. 3, 2008 in U.S. Appl. No. 10/473,999.
Reply to USPTO OA of Jun. 14, 2006 in U.S. Appl. No. 10/492,753.
Reply to USPTO OA of Feb. 21, 2007, in U.S. Appl. No. 10/492,753.
Reply to UPSTO OA of Oct. 16, 2007, in U.S. Appl. No. 10/492,753.
Reply to USPTO OA of Oct. 6, 2008, in U.S. Appl. No. 10/492,753.
Office action mailed Oct. 25, 2011 in U.S. Appl. No. 10/492,753.
Reply filed Jan. 24, 2012 in U.S. Appl. No. 10/492,753.

* cited by examiner

PLATE FOR OSTEOSYNTHESIS DEVICE AND METHOD OF PREASSEMBLING SUCH DEVICE

The present invention relates to an osteosynthesis device, particularly for spinal support or correction, enabling easier and compact implantation, that can be particularly used in the case of implantation via the anterior approach, and a preassembly method for such a device.

For spinal support or correction, a device comprising a supporting element comprising one or more support bars or plates positioned along the spinal column is used, and fixed to certain vertebrae by implants. Said implants are fixed at one end to the plate and at the other end to the vertebrae by bone anchorage means, for example a threaded part screwed inside the actual vertebra.

In such devices, it is known to use a plate comprising several holes, to join the implants fixed to several vertebrae, as described in the patent FR2726171, for example. Said bars then surround or pass through the head of the screw and are locked with a nut screwed onto said head.

However, such a device requires that the clamping nut only be fitted on the screw after the screws and the plate have been positioned. Therefore, said nut can only be inserted onto the screw head during the operation, with all the difficulties and risks of loss that may be caused by handling and assembling a small part inside a human body. This operation is all the more problematic when said operation is conducted by means of endoscopy, for example when it is necessary to implant via the anterior approach, i.e. via the front of the body or on the front face of the spine.

A device according to the prior art also requires that the implants be fixed and completely clamped before the plate is positioned. Therefore, in the event of delicate operative conditions, it is difficult to successfully position the plate very close to the spine. This problem arises for example when. The shape of the spine comprises too many irregularities, due to spinal displacement or deformation or in the presence of outgrowths such as osteophytes. There are similar problems in the case of implantation by the anterior approach, i.e. via the front of the body or on the front face of the spine. Indeed, the anatomical conditions in this case frequently only leave space for a compact size. In addition, it is often necessary to work by means of endoscopy in this case, which renders the operation difficult and gives a less satisfactory view of the implant insertion depth.

In some cases, to enable subsequent consolidation of the fixation between the implant and the vertebra, an implant composed of a so-called if "rehabitable" screw is used, i.e. a hollow screw wherein the inside communicates with the outside via openings passing through the threaded wall. During the screwing into the vertebra, part of the bone substance penetrates inside the screw. Over time, the bone substance fuses between the inside and outside of the screw via these openings, thus forming consolidation over time.

In this way, the patent FR 2726171 discloses a hollow screw wherein the openings are produced by cutting on the inner surfaces of said screw longitudinal grooves which cut into the base of the outer threading. However, during positioning or subsequently, such a screw may form anchoring which is not sufficiently strong and is liable to be dislodged or torn from the vertebra wherein it is implanted.

One of the aims of the invention of the invention is to provide a plate that can be fitted on preassembled implants already screwed into the spine.

Another aim of the invention is to provide an osteosynthesis device that can be partly preassembled before the operation to enable easier implantation.

In this way, the invention relates to a device as described above, wherein the plate has an elongated shape and comprises, on at least one of its ends, at least one longitudinally elongated opening. The opening has at least one part opening onto an edge of the plate, or one part of a sufficiently large size as to be inserted without disassembly in an attachment structure of an implant that had been previously screwed into the spine when said attachment structure are already assembled. The opening also has one part having a substantially constant width and that is able to slide longitudinally in the attachment structure of said implant after having been inserted and of being disposed thereon. Such a plate can thus be assembled by disposing one end to an already fitted implant, and then sliding in the attachment structure of said implant to insert the other end in another already fitted implant. The plate is then again slid to bring both ends into the attachment position. The attachment structure of the two implants were assembled before being attached to the spine.

One aspect of this invention constitutes an osteosynthesis device having a plurality of implants that are each adapted to be joined to one or more vertebrae. When thus joined to a vertebrae, these implants a substantially rigid point of attachment between the implanted vertebrae and at least one support element. The support element is made up of at least one plate or bar. The assembly of the supporting element(s) and the implants are adapted to hold a spine in place, or to displace a spine from an improper alignment into a more correct alignment. The supporting element(s) is joined to at least two of the implants by an attachment structure. The supporting element has an elongated shape wherein at least one of its ends has at least one longitudinally elongated opening. At least one opening extends to an edge of the plate, or is an aperture of a sufficiently large size to accept the insertion of the exposed part of the implanted attachment member which is sized to be able to be inserted, without disassembly, to the support member through the hole. In this arrangement, the implant that has previously been attached to a vertebrae of the spine. A part of the aperture has a substantially constant width that is able to slide longitudinally on to the attachment structure of the implant after the implant has first been inserted and of fixed to the support structure. One end of the support plate is adapted to be assembled at one end to first implant that has been attached to a vertebrae, and is adapted to then be caused to slide in relation to the attachment structure of the first implant so as to enable the other end of said plate to be attached to a second implant that has previously been joined to a vertebrae (preferably a different vertebrae), and is adapted to then be slid again in order to bring both ends of said plate into attachment to the respective attachment structures.

According to one embodiment, the plate comprises two parts having identical lengths or not. The two parts are joined together by a joining part that is located in an inner part of the plate, i.e. at a sufficient distance from the plate ends to enable the plate to be attached onto two implants so that one implant is on each side of said joining part.

According to one embodiment, the joining part is located in a position offset with respect to the center of the plate length.

According to one embodiment, the plate has an "H" or "h" shape.

According to one embodiment, the plate has at least one longitudinally elongated opening having a first constant width region and a second region that is larger in size than the first region. The opening is large enough to allow the attachment structure of an implant to pass through the plate before sliding to bring the attachment structure into the first region.

Another aim of the invention is to propose a compact osteosynthesis device, that can be fitted and adjusted in a position very close to the spine.

This aim is achieved by an osteosynthesis device, particularly for the spine, comprising a plurality of implants that can be screwed into one or more vertebrae and provide a rigid joint between said vertebrae and at least one plate or bar used to hold or displace the spine, characterized in that the plate is joined to at least one implant by fixation means able to hold said plate without preventing the implant from rotating on its screwing axis, or without preventing a specified clearance of the plate with respect to the implant, or both: thus making it possible to continue screwing the implant, or adjust the position of the plate, or both, after the plate has been assembled on the implant.

According to one embodiment, at least one implant has an elongated shape around an axis, referred to as the implant axis, and comprises a first bone anchoring end bearing at least one threading and a second end with an elongated part passing through a plate support, said plate support being free in rotation around said elongated part, said elongated part bearing clamping means able to hold and clamp the plate against said plate support.

Another aim of the invention is to propose an osteosynthesis device that can be screwed or clamped when it is not possible to use a tool in the actual axis of the implant.

This aim is achieved by a device as described above, characterised in that the elongated part, referred to as the clamping support, of the implant is mobile with respect to the rest of the implant, along a universal type joint between a part of the implant referred to as the screw head and a part of the clamping support referred to as the support head, thus making it possible to continue screwing the implant after the plate has been assembled on the implant, by rotating the clamping support around a clamping support axis, when said axis forms a non-null angle with the axis of the implant.

According to one embodiment, the plate surrounds the clamping support or the second end of the implant at least partly and rests on a surface of its complementary plate support, said plate support having on the implant side a concave surface in the form of a spherical portion which is supported in a complementary fashion on the outer surface of the implant screw head.

According to one embodiment, the clamping support has a first elongated end along the support axis and a second end bearing the support head, said support head having a non-circular cross-section having at least one concave part and comprising at least one dimension greater than at least one cross-section of the first end of the clamping support; said support head having firstly one section roughly partly circular along a plane including the support axis, and being secondly arranged in the screw head inside a housing wherein the inner surface has at least one projecting part cooperating with the concave part of the support head to prevent rotation of the clamping support around its axis.

According to one embodiment, the inner surface of the screw head housing has a shape substantially complementary to the outer surface of the support head.

According to one embodiment, the housing receiving the support head has, on the side of said clamping head, a specified dimension to allow the clamping support a clearance along a specified angle, between the axis of the clamping support and the axis of the implant, without said clamping support escaping from said housing.

According to one embodiment, the clamping support head has a star-shaped cross-section with rounded ends, along a plane perpendicular to the support axis.

According to one embodiment, the clamping support clamping means comprise a threading that is adapted to cooperate with a nut to hold or clamp the plate against the plate support.

According to one embodiment, the clamping support comprises at its end opposite the implant an inner or outer recess capable of receiving a rotational drive tool and thus enable the complete screwing or clamping of the implant in the vertebra.

One of the aims of the invention is to propose an osteosynthesis device enabling improved screw implantation strength, during fitting, during the period prior to bone fusion or after consolidation.

This aim is achieved by a device such as that described above, characterized in that the first bone anchorage end of at least one implant has a longitudinal bore concentric to its outer surface, said bore communicating with the outside by at least one bone fusion opening disposed in the wall between said inner bore and said outer surface, thus enabling a fusion, of the bone substance in contact with said first end, between the inside and the outside.

According to one embodiment, the first bone anchorage end of at least one implant has two threadings that wind in the same direction during the screwing of the implant. These are borne respectively by the outer surface of said first end and the inner surface of the bore that it comprises.

According to one embodiment, at least one bone fusion opening has the shape of a longitudinal oblong hole.

Another aim of the invention is to provide a preassembly method for such an osteosynthesis device.

This aim is achieved by the preassembly method for a device according to the invention, characterized in that it comprises the following steps:
  assembly of the plate support on the clamping support of an implant; and
  assembly of the nut on the thread of the clamping support of said implant.

BRIEF DESCRIPTION OF THE DRAWING FIGURES

The invention, with its characteristics and advantages, will be seen more clearly upon reading the description with reference to the appended figures wherein.

DETAILED DESCRIPTION OF THE INVENTION

Figure 2:
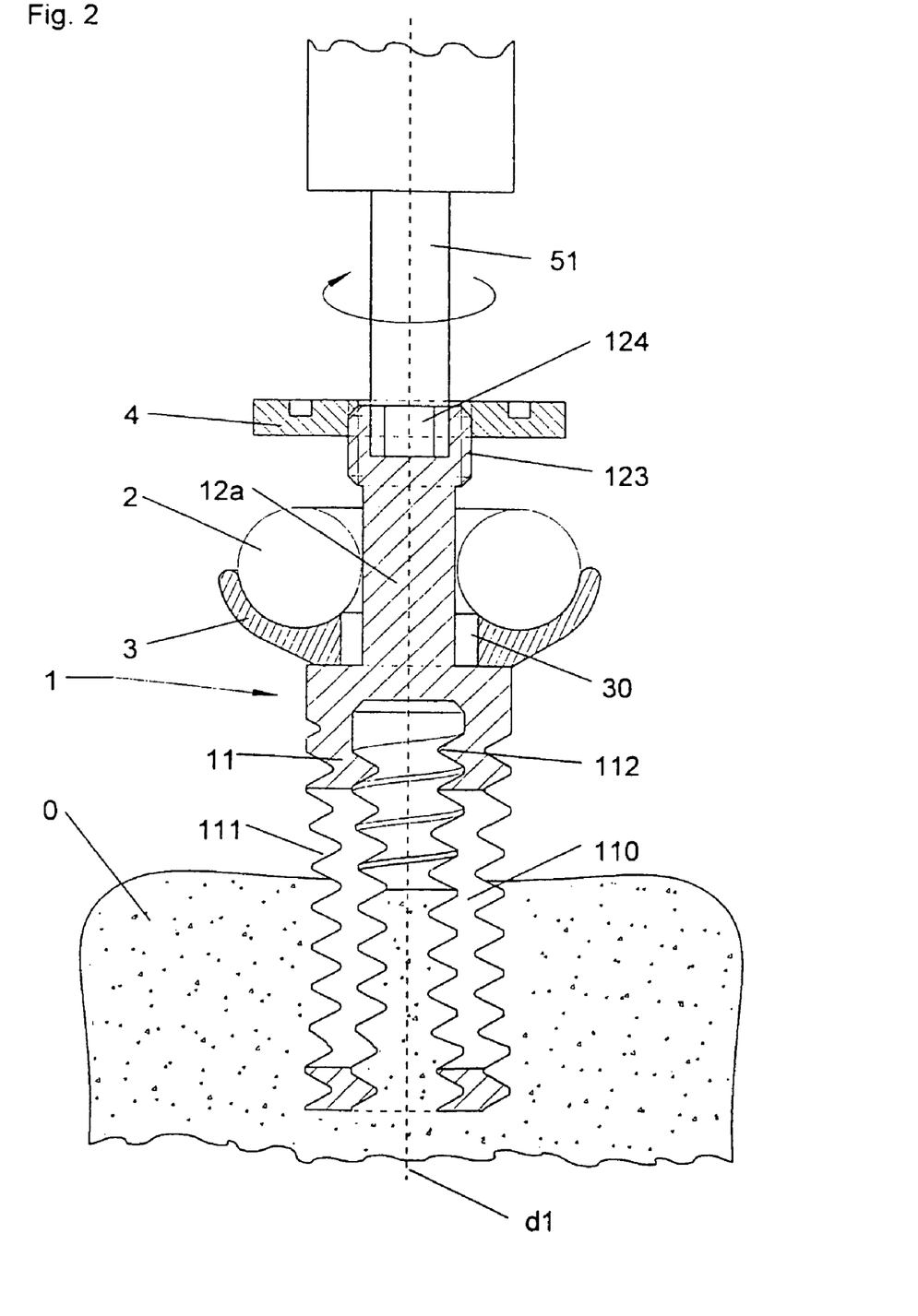
FIG. 2 represents a longitudinal section view of an implant of a device according to the invention in the implant clamping phase after insertion of the plate, in an embodiment comprising a plate support free to rotate around a rehabitable hollow screw implant and fixed clamping support.

In an embodiment represented in FIG. 2, the device according to the invention comprises an implant 1 comprising a first end 11 equipped with an outer threading 111, and is illustrated after a first having been screwed in the bone substance of a vertebra 0, after insertion of a plate 2 and during the final approach. Said first end 11 also comprises a cavity or an inner bore, itself equipped with an inner threading 112 wherein the screwing direction is the same as that of the outer threading 111. During the screwing of the implant into the vertebra 0, part of the bone substance tends to fill said cavity and is assisted therein by the action of the inner threading. Preferentially, the inner threading 112 and the outer threading 111 are of the same pitch, so as to minimise the strain exerted on the bone substance at the entry of the bore during screwing.

The wall between the inner cavity and the outside of the implant has one or more openings, referred to as bone fusion holes 110, in its part which is inside the vertebra after the attachment of the implant. In the time period following the implantation, generally approximately six months, the bone substance present outside and inside the implant tends to fuse. The fusing produced in this way improves the strength of said implantation, both by means of blocking via the bone fusion holes 110, and by means of cooperation of the inner threading 112 with the bone pin formed in this way.

In one alternative embodiment, the inner threading 112 has a greater pitch than that of the outer threading 111. During the screwing of the implant 1, the bone substance present inside the cavity is then attracted slightly more quickly than the implant progresses in the vertebra 0. This effect may make it possible to compensate for a filling defect liable to occur, for example by compression of the bone substance inside the bore. This effect may also make it possible to obtain more complete or more compact filling of said cavity, for example in order to obtain a specific compression or better filling of the cavity or the bone fusion holes 110, and thus fabor bone substance fusion.

At its second end, i.e. the end opposite the vertebra, the implant 1 comprises an attachment structure that is used to insert, hold and finally clamp a bar or a plate 2. Said second end also comprises a receptacle for a drive means, using a tool of known type, such as a hexagonal recess 124.

Said attachment structure comprises for example an elongated part 12a of a cross-section less than the central part of the implant, comprising a shoulder. Said elongated part 12a passes through a plate support 3 resting on said shoulder, and comprises at its end a threading 123 adapted to receive a clamping nut 4. In one embodiment, said plate 2, as shown in FIG. 5a, is roughly "H"-shaped, comprising for example two cylindrical bars joined at their center by a rigid distance sleeve. In an alternative embodiment, the two bars are joined by a non-rigid joint. Because the joint is not rigid, it allows more latitude in the positioning of the plate. Said plate 2 is inserted between the plate support 3 and the nut 4, so as to surround the elongated part 12a of the implant. Once the plate is in position, the nut 4 is fastened, by hand or using a tool of a known type 52, FIG. 4, and cooperates with the threading 123 to clamp the plate 2 against the plate support 3 and thus lock the assembly.

In said embodiment, the plate support 3 comprises a bore 30 with a substantially rectangular insert passing through its center. Said plate support 3, on the side of the plate, has one or more surfaces 2 that are substantially complementary to the surface of the plate 2 resting on them. In said embodiment, the central bore of the plate support 3 is sufficiently larger than the part 12a passing through it to allow a clearance of said support 3 transversally and at an angle with respect to the axis d1 of the implant. Said clearance makes it possible to adjust the relative position of the plate supports of two implants 1, 1a easily, and thus insert the plate 2 easily even if the implants are not well aligned or in the event of a relatively inaccessible anatomical environment. According to an alternative embodiment not shown, the plate support receives a plate 2a, FIG. 5b, comprising a single bar at one of its ends. Said plate support can then comprise an offset bore instead of the central bore 30, without departing from the scope of the invention.

Since the plate support 3 is free to rotate around the part 12a of the implant 1, it is clearly understood that it is possible to continue screwing said implant into the vertebra 0, even when the plate is already in position, provided that the attachment structure is not firmly fastened on said plate 2. In this way, by inserting the plate 2 into said attachment structure before the implant 1 is entirely screwed on, it is possible not to be hindered by the various differences in levels or outgrowths liable to be present in the immediate vicinity of the spine. Once the plate is held in place but not clamped, it is still possible to finish screwing the implant into the vertebra, by rotating it via an opening of the plate support 3. The attachment structure then holds the plate 2 close to the spine, the screwing of the implant providing sufficient force to oblige the plate to come closer to the spine. Therefore, the plate can be positioned and inserted with little effort, while being positioned definitively very close to the surface of the vertebra, which makes it possible to obtain a compact device size once fitted.

Figures 3, 3A:
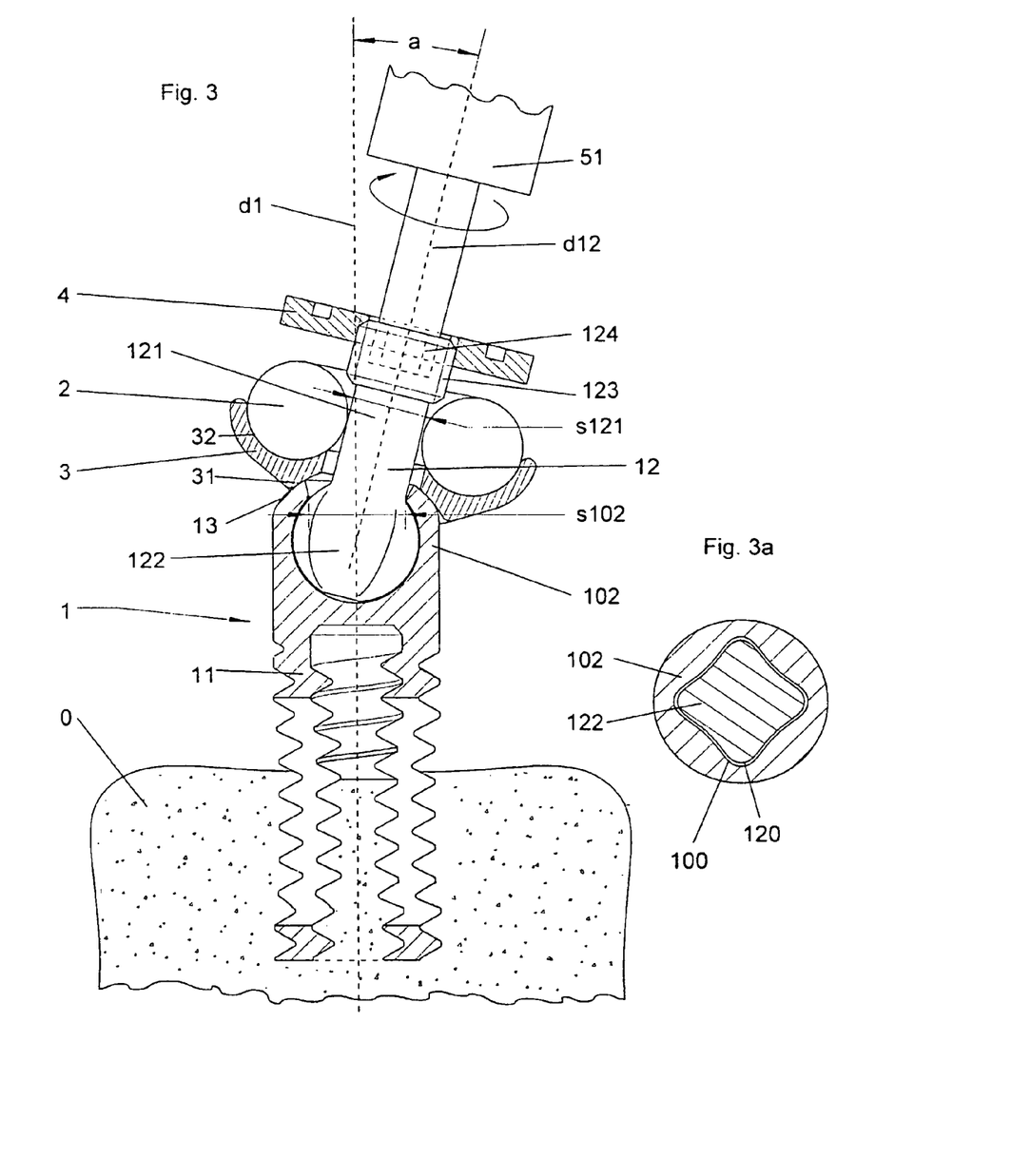
FIG. 3 represents a longitudinal section view of an implant of a device according to the invention in the implant clamping phase after insertion of the plate, in an embodiment comprising a plate support free to rotate around a rehabitable hollow screw implant and inclinable clamping support.
FIG. 3a represents a partial view of an implant according to the invention, in a section along a plane passing through the centre of the support head and perpendicular to the support axis.
Figure 4:
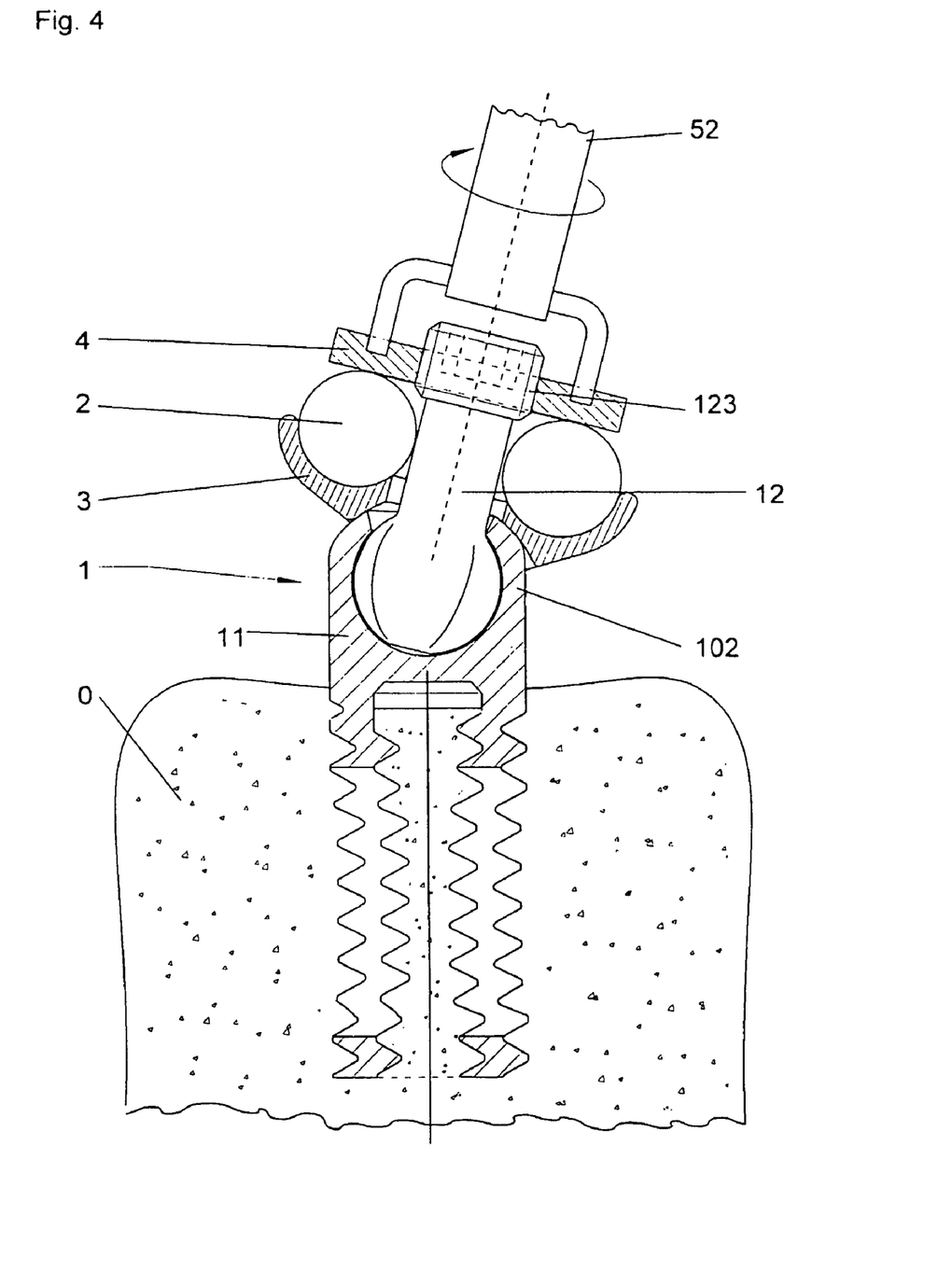
FIG. 4 represents a longitudinal section view of an implant of a device according to the invention in the plate clamping phase once the implant is in its definitive position, in an embodiment comprising a plate support free to rotate around a rehabitable hollow screw implant and inclinable clamping support.
Figure 5A:
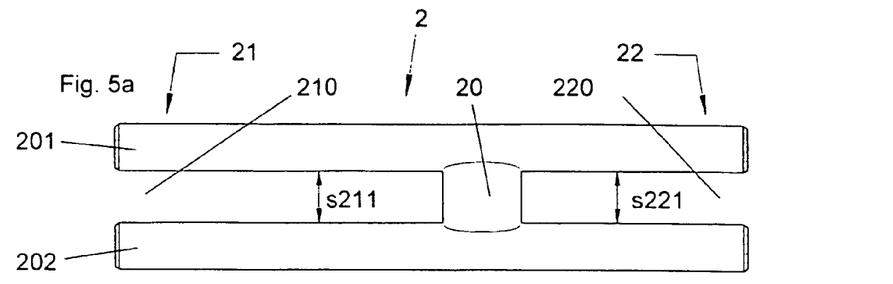
FIGS. 5a, 5b, 5c and 5d represent a top view of a plate of a device according to the invention, in an embodiment comprising a plate which is respectively "H"-shaped with two through openings, "h"-shaped with one through opening, with two non-through openings and with one non-through opening.

In a preferential embodiment of the device according to the invention, represented in FIGS. 3, 3a and 4, the implant 1 comprises a mobile part, referred to as the clamping support 12, at its second end opposite the first end 11 screwing into the vertebra 0. Said clamping support 12 has an elongated first end 121 along a support axis d12. Said elongated end passes through the central bore of the plate support 3 and bears a threading 123 adapted to receive the clamping nut 4.

At a second end opposite its elongated end 121, the clamping support 12 bears a part, referred to as the support head 122, joining said clamping support 12 to the implant by its second end, referred to as the screw head 102, opposite the end 11 screwed into the vertebra 0. Along a plane perpendicular to the support axis d12, said clamping support head 122 has at least one dimension s122; FIG. 3*a*, greater than at least one cross-section s121 of the elongated end 121 of said clamping support 12. Said support head 122 is retained in a housing provided in the screw head 102 of the implant 1. For this purpose, said housing has an opening of a specified size s102 so as to retain the support head 122 inside said housing, while allowing a clearance of a specified angle a between the support axis d12 and the implant axis d1.

Said angular clearance of the clamping support 12 with respect to the implant enables angular and lateral movements facilitating the insertion of the plate in the fixation means of the implant, as described below. Said angular clearance also makes it possible to compensate for any alignment defects between the different implants 1, 1*a*; FIG. 1*c*, of a device according to the invention and therefore renders the positioning of the plate 2 in the attachment structure of said implants less delicate.

In said preferential embodiment, the plate support 3 rests on the screw head 102 of the implant 1, by means of a lower surface 31 that has at least a partially spherical surface for example. Said lower surface 31 of the plate support is in complementary contact with an upper surface 13 of said screw head. Said spherical complementary contact allows freedom of rotation and inclination of the plate support 3 with respect to the implant 1. Said spherical complementary contact of said surfaces 13, 31 also enables a uniform and stable support of said surfaces with respect to each other, after the plate 2 has been clamped onto the plate support, irrespective of the definitive angular position of said plate support 3 or the clamping support 12.

The implant 1 is screwed into the vertebra 0 by means of rotationally driving said implant by rotating the clamping support 12 around its own clamping axis d12. Said clamping support is rotated for example by a tool, of known type, inserted into at least one recess 124 contained in the elongated end 121 of said clamping support. The clamping support 12 preferably rotates the implant 1 by means of a universal type joint, i.e. the rotation of either of the two components around its axis rotates the other component around its own axis, the angle between the two axes possibly being non-null.

Said universal joint is produced by the cooperation of the outer surface 120 of the support head 122 with the inner surface 100 of the housing of the screw head 102 of the implant 1. Along a plane perpendicular to the support axis d12, the support head 12 has a section with a non-circular outline, for example in the shape of a star or cross with rounded corners, as illustrated in FIG. 3*a*. The housing of the screw head 102 which receives the support head 122, then has an inner surface 100 in substantial complementary contact with the outer surface 120 of said support head 122, said two surfaces 100, 120 cooperating to form the rotational joint between these two components 102, 122. The angular variation is allowed by the fact that the support head 122, and its complementary housing, have a section with a circular outline along at least one plane including the clamping support axis d12, or the implant axis d1, or both.

Figure 7A:
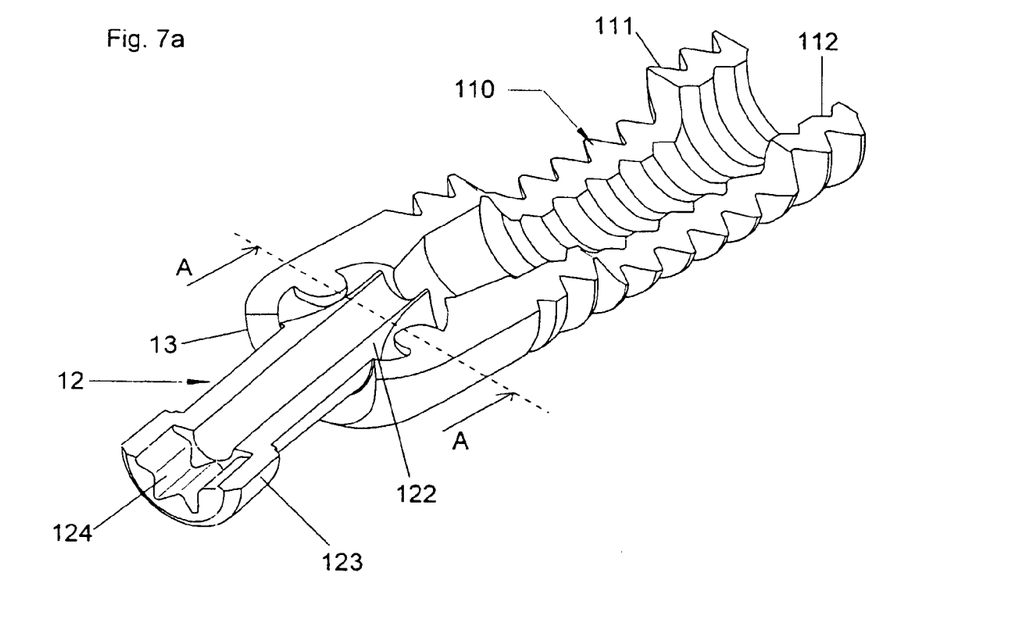
FIG. 7a represents a perspective view of a longitudinal section of an implant of a device according to the invention, in an embodiment comprising an inclinable clamping support and a rehabitable hollow screw with two oblong holes and according to an alternative embodiment where the screw head housing and the support head interact without being complementary in shape.
Figure 7B:
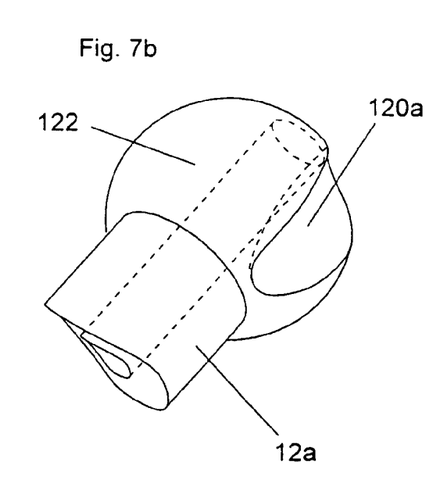
FIG. 7b represents a partial perspective view of the support head of an implant of a device according to the invention in the same alternative embodiment.
Figure 7C:
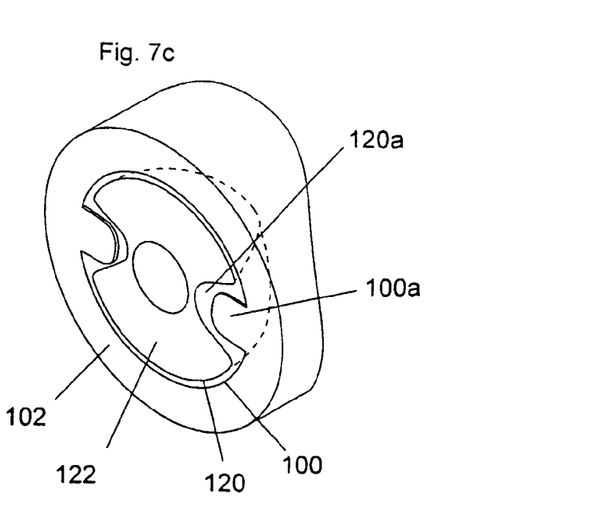
FIG. 7c represents a partial perspective view of a cross-section along the plane AA (as shown in FIG. 7a) of an implant of a device according to the invention in the same alternative embodiment.

According to an alternative embodiment illustrated in FIGS. 7*a* to 7*c*, the inner surface 100 of the screw head housing receiving the support head simply has one or more projecting parts 100*a*, for example two. The outer surface 120 of the support head 122 then has one or more concave parts 120*a* with which the projecting parts 100*a* of the screw head housing cooperate to prevent the rotation of the clamping support 12 around its axis d12.

In this way, it is clear that it is possible to continue screwing the implant 1 into the vertebra 0, after the plate 2 has already been inserted between the clamping nut 4 and the plate support 3, by adjusting the elongated end 121 of the clamping support 12 that is accessible via the nut 4. Since the plate support 3 is free to rotate with respect to the implant 1, said implant can rotate during screwing while leaving the plate 2 and the plate support 3 immobile.

Once the implant 1 is completely screwed into the vertebra 0, as illustrated in FIG. 4, the plate 2 can then be adjusted and locked in its definitive position, by tightening the clamping nut 4. Said nut may be tightened by hand, for example on a knurled part of its outer surface on the support axis d12, or using a tool 52 of known type, for example by adjusting two inner or outer recesses on the nut.

Figure 8:
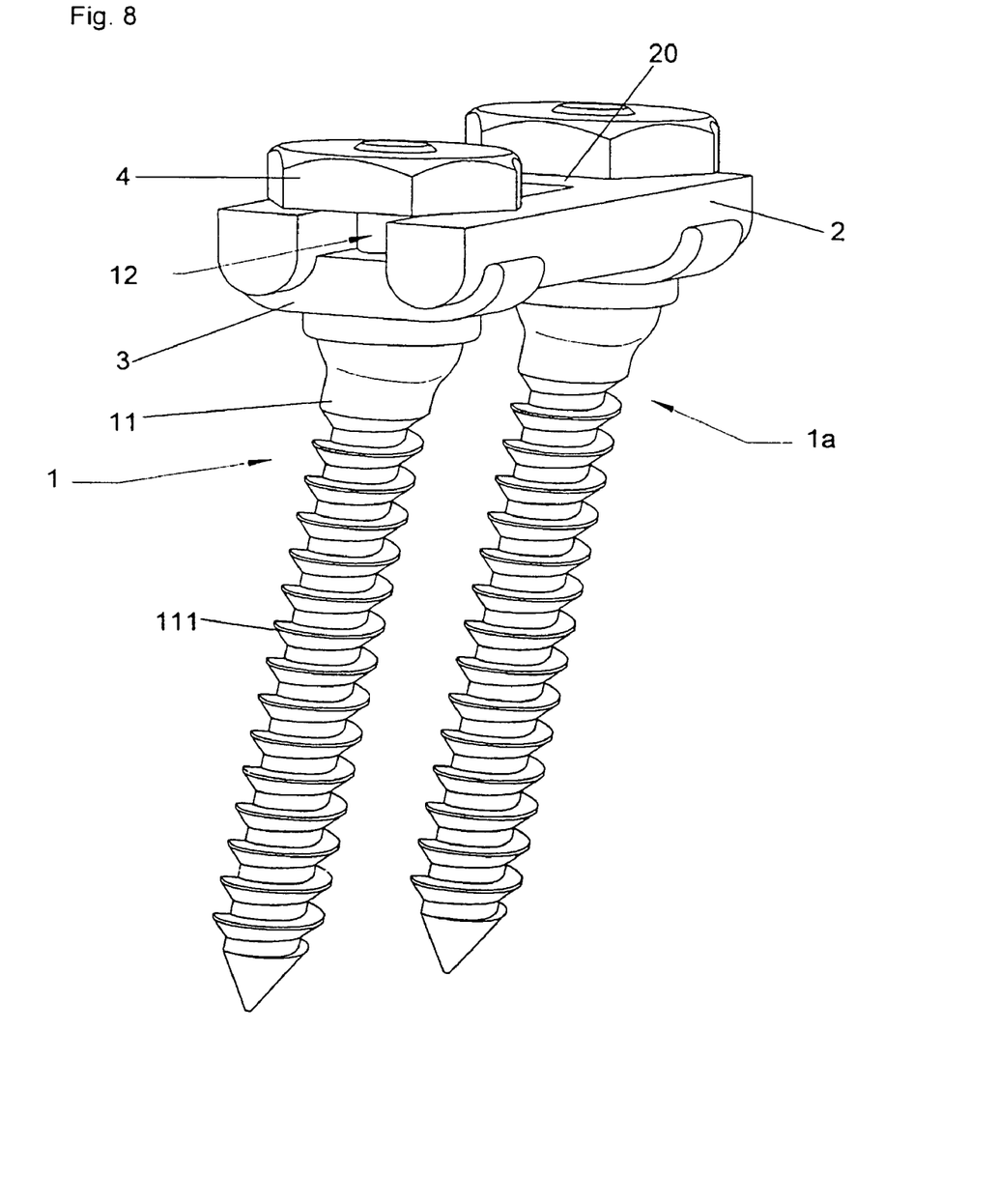
FIG. 8 represents an osteosynthesis device according to the invention in an embodiment comprising an "H"-shaped plate and two polyaxial head implants according to an alternative embodiment where the implants only comprise a single threaded part, on their outer surface.

According to an alternative embodiment illustrated in FIG. 8, a device according to the invention uses such implants but wherein the end 11 intended to be anchored in the vertebra only comprises one outer threaded part 111. In said alternative embodiment, the implant may comprise a longitudinal bore passing through it from one end to another, to enable positioning by means of sliding around a pin that has previously been implanted in the vertebra.

Several implants according to various alternative embodiments in the same device can of course be combined without departing from the scope of the invention.

Depending on the applications, in order to join two implants 1, 1*a*; FIG. 1*c*, it is possible to use a plate of different configurations, for example such as those represented in FIGS. 5*a*, 5*b*, 5*c* and 5*d*.

Figure 1A:
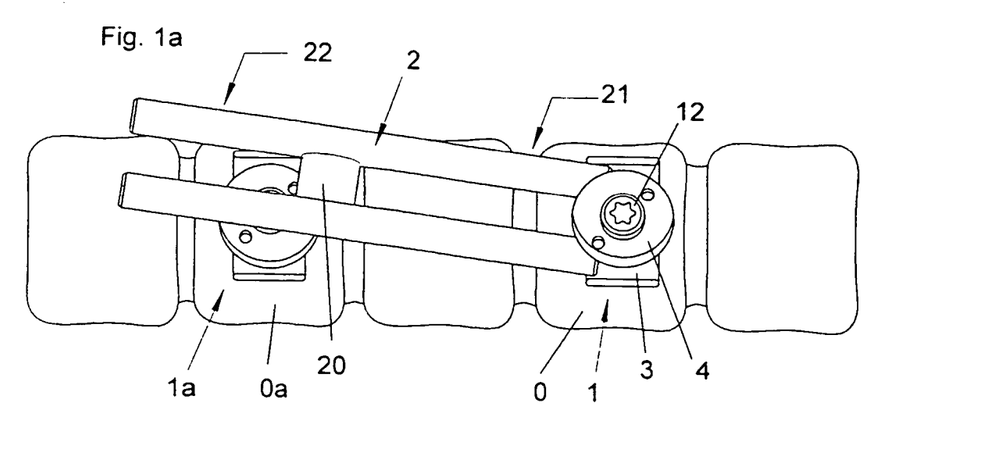
FIGS. 1a, 1b, and 1c represent an osteosynthesis device according to the invention in an embodiment comprising an "H"-shaped plate and two polyaxial head implants fitted on an interval vertebra, in three successive phases of the fitting of the plate in the implants.
Figure 1B:
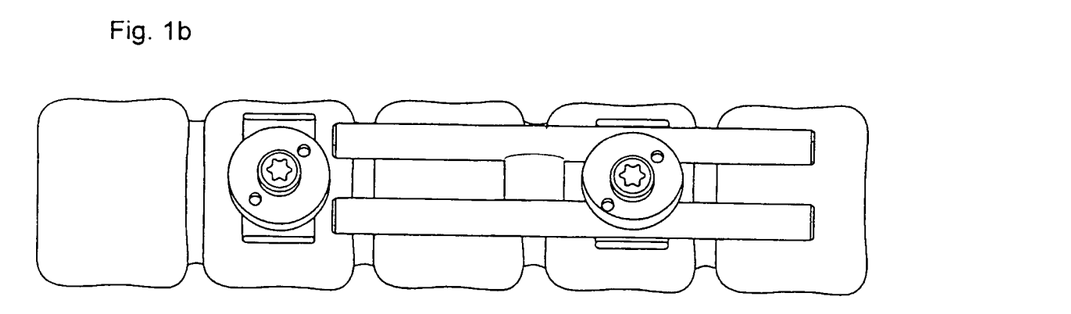
Figure 1C:
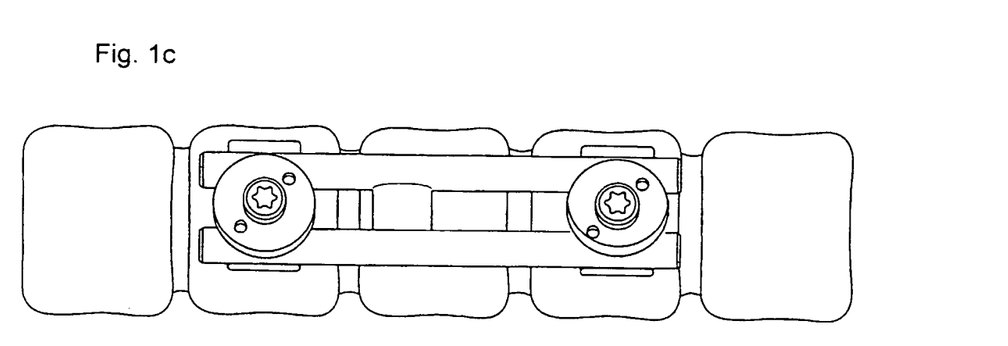

In the example of an embodiment illustrated in FIGS. 1*a*, 1*b*, and 1*c*, two implants 1, 1*a* are screwed into the body of two, respective, vertebrae 0, 0*a* respectively of the spine, spaced at an interval of one vertebra. These two implants are then fixed together by a plate 2 inserted into their attachment structures around the clamping support and then clamped between the plate support and the nut of each of said implants.

In the preferential embodiment represented in FIG. 5*a*, the plate 2 is elongated in shape and comprises two roughly parallel bars 201, 202, which are for example cylindrical, joined together in a rigid or flexible manner by a joining part 20. Said joining part joins the two bars at an inner part of the plate, i.e. at a specified non-null distance from each of the ends 21, 22 of the plate. More specifically, said joining part is located at a sufficient distance from each end of the plate so that said end can be inserted into the fixation means of an implant, and possibly slide in said attachment structure. The position of said joining part 20 may be located at the center of the plate, or be offset to allow a greater clearance for sliding during insertion as explained below.

At each end 21, 22 respectively, of the plate 2, the space between the two bars forms an opening 210, 220 respectively, opening out onto the edge of the plate. Said openings have a substantially constant transverse gap s211, s221, enabling longitudinal sliding of the plate in the attachment structure of an implant 1, 1*a*. This substantially constant transverse gap also makes it possible to clamp said attachment structure in any part of said openings 210, 220. Since said openings open onto the edge of the plate, it is possible to insert each of the ends of the plate into the attachment structure of an implant 1, 1a as illustrated in FIG. 1a, without having to remove the nut 4 if it was preassembled beforehand. At each end, this insertion consists of sliding the end of the two bars between the nut 4 and the plate support 3 of the implant 1, at either side of the clamping support 12.

Figure 5B:
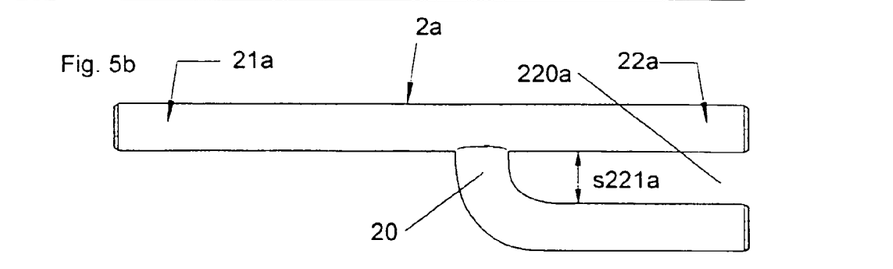

In another embodiment represented in FIG. 5b, the plate 2a is elongated in shape and comprises a first end 21a comprising a single bar, which is cylindrical for example. Said first end can be inserted into an implant according to the prior art or into an implant as described in the present invention, for example in an alternative embodiment (not shown) where the plate support only comprises a single surface 32 in contact with the plate. The plate 2a also has a second end 22a comprising two substantially parallel bars, which are cylindrical for example. These two bars together form a longitudinally elongated opening 220a, of a roughly constant width s221a. Either of the two ends of said plate 2a can be inserted, or slid, or both, in the attachment structure of an implant according to the invention, in the manner described in the preferential embodiment.

Figure 5C:
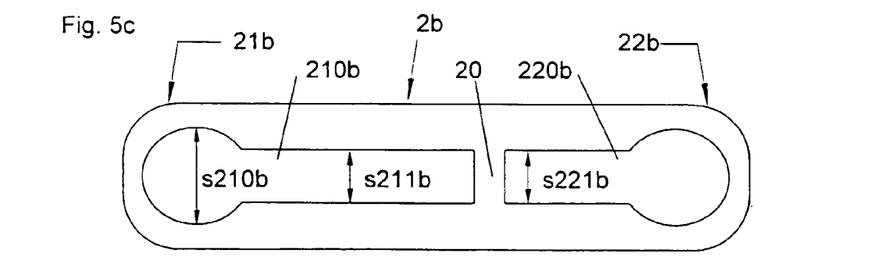

In another embodiment represented in FIG. 5c, the plate 2b is elongated in shape and comprises a first end 21b having at least one opening 210b and a second end 22b having at least one second opening 220b, at least one of these openings not opening onto the edge of the plate 2b. These two openings 210b, 220b have a longitudinally elongated shape, i.e. along the length of the plate, and may be separated by one or more joining parts 20. These two openings have a substantially constant width s211b, s221b, and can be positioned by means of sliding and then be clamped in the attachment structure of the implants. At least one of said openings has a part, referred to as a notch, of a larger size s210b, s220b, of a shape and size able to allow the nut 4 of the attachment structure of an implant to pass through. Therefore, such a bar 2b can also be inserted in the attachment structure of an implant 1 when said attachment structure is already assembled, therefore not requiring handling of small parts, such as the nut 4 or the plate support 3, in the patient's body.

Figure 5D:
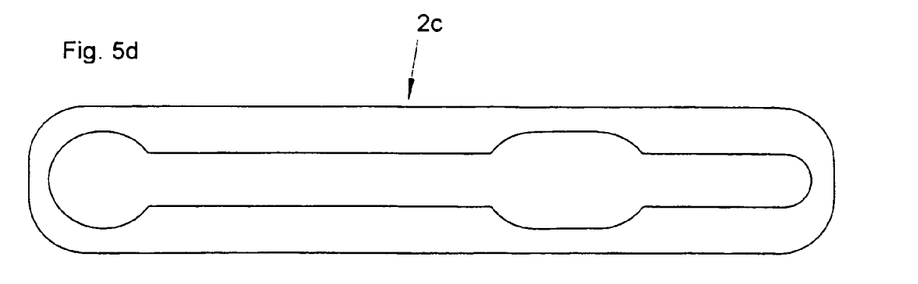

In an alternative embodiment represented in FIG. 5d, the plate 2c has a single opening comprising two notches as described above (see FIG. 5c). In an embodiment not shown, the plate may comprise a sufficient number of openings and notches to be able to assemble the plate to more than two implants.

It is clear that these different types of openings, which are either through apertures or have a wider part, can be combined in various ways without departing from the scope of the invention.

In the same way, the position of the joining part 20 can vary and be offset along the length of the plate, so as to leave the clearance required for the plate to slide during positioning. In a preferential embodiment, said position is slightly offset with respect to the center of the plate, so as to be able to slide the plate sufficiently in the first implant 1; FIG. 1b, to be able to have the second implant 1a inserted into it.

It is necessary to understand here that the device described can equally well comprise any other combination of different alternative embodiments of plates and alternative embodiments of implants without departing from the scope of the invention.

FIGS. 1a, 1b, and 1c illustrate different steps in the positioning of the plate 2 in two implants 1, 1a, in the preferential embodiment. This positioning is carried out after the implants have already been screwed into the spine, and where the attachment structures, in this case the plate support 3 and the nut 4 have already been assembled on the implant but not yet fully clamped.

In this way, in FIG. 1a, a first end 21 of the plate 2 is first mated with the attachment structure of the first implant 1, on the plate support 3 and under the nut 4, straddled around the clamping support 12.

Once this first end 21 has been inserted, due to the fact that the bars have a substantially constant gap, it is possible to slide the plate in the attachment structure of the first implant 1 until the second end 22 of the plate can be aligned (FIG. 1b) in front of the attachment structure of the second implant 1a.

By sliding the plate in the opposite direction, it is then possible to insert (FIG. 1c) said second end 22 in a similar manner in the attachment structure of the second implant 1a. It is them possible to adjust the definitive position of the plate 2 and tighten the nut of the attachment structure of each of the two implants, and thus stiffen the assembly.

In this way, it is clear that it is possible to prepare the osteosynthesis device in advance using the preassembly method, comprising the following steps:
  assembly of the plate support 3 around the clamping support; and
  assembly of the nut 4 on the threading 123 of the clamping support.

Figure 6:
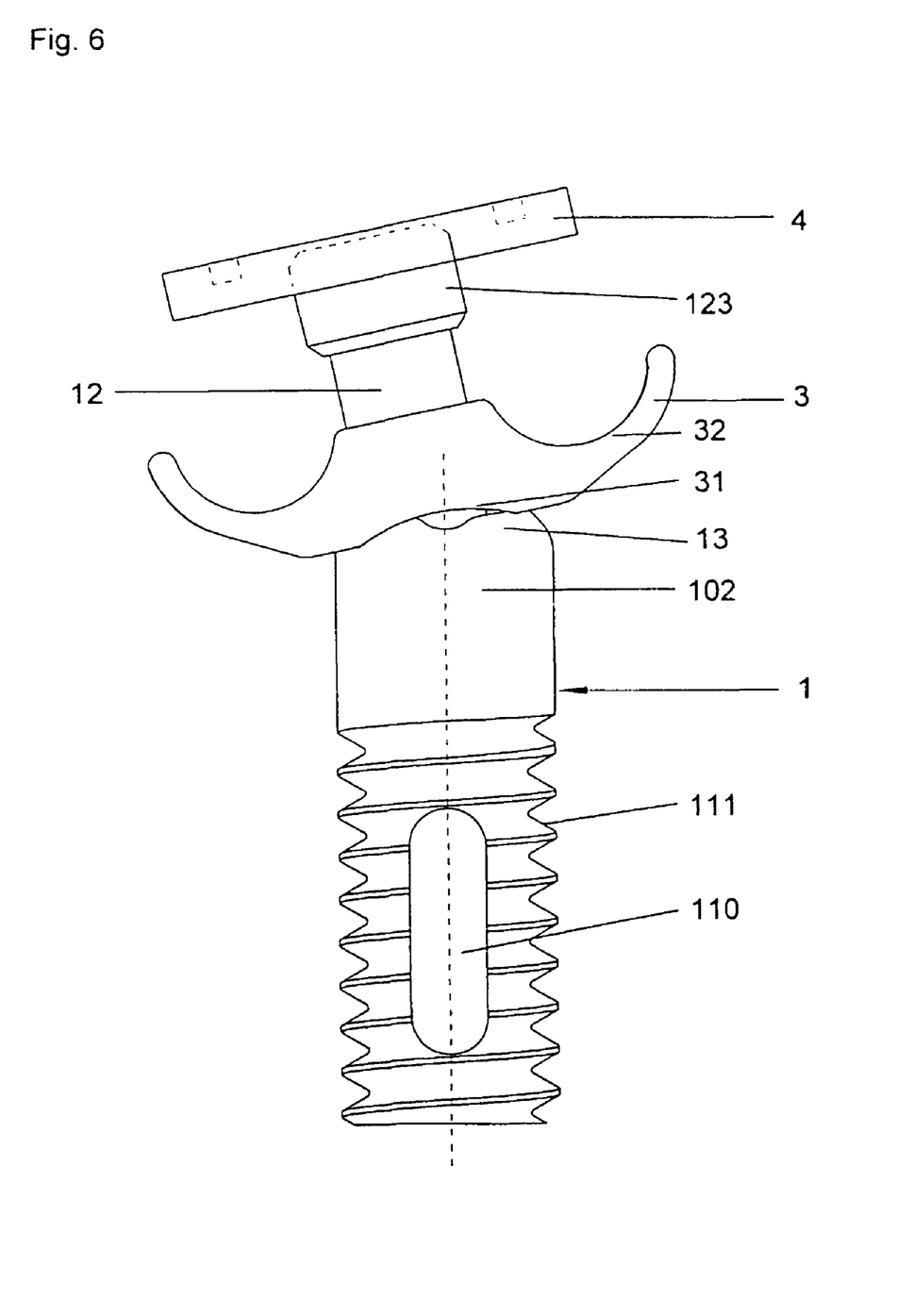
FIG. 6 represents a side view of an implant of the preassembled device according to the invention, in an embodiment comprising an inclinable clamping support and a rehabitable hollow screw with two oblong holes.

Once it has been preassembled using this method, an implant 1 of the device according to the invention can be used directly during the surgical operation, as represented in FIG. 6.

The osteosynthesis device can then be positioned using the following steps:
  the implants are screwed into the spine, without inserting them to their final depth. This approach position makes it possible not to be hindered by any osteophytes when positioning the plate 2.
  The plate 2 is inserted via a first end 21 into a first implant 1. It is then slid into said first implant to be presented in front of the attachment structure of the second implant 1a. The second end 22 is then inserted into the second implant. This positioning is illustrated in FIGS. 1a, 1b, and 1c.
  At this stage and subsequently, the clearance of the plate support 3 around the clamping support 12 allows the angular and lateral movements required for insertion. This clearance also makes it possible to compensate for any alignment defects between the two implants 1, 1a, and thus renders the positioning of the plate 2 less delicate.
  The screwing of the two implants into the spine is then completed until they are clamped in their final desired position. This screwing is performed (FIG. 3) using a tool of known type, such as, for example, drive tool 51 shown in FIGS. 2 and 3, rotating the implant by means of a rotation of the clamping support 12. Since the plate 2 is already in position and held in place by the attachment structure of the implants, this additional screwing of the implants drives the plate to its desired final position close to the spine. Therefore, this driving obtained by screwing the implants makes it possible to reduce the size determined by said plate, by tightening or inlaying said plate firmly and easily on the surface of the spine.
  Once the implants have been completely screwed on, the plate is locked in the attachment structure of the implants, by clamping (FIG. 4) their nut 4 on the plate 2 itself resting on the plate support 3 which rests on the shoulder or on the screw head 102 of the implant. Naturally, said clamping may be carried out using other parts not mentioned, such as washers or locking devices of known types.

It must be clear to those skilled in the art that the present invention enables other embodiments in numerous other specific forms without leaving the scope of the invention as claimed. As a result, the present embodiments must be considered as illustrations, but may be modified in the field defined by the scope of the fixed claims, and the invention must not be restricted to the details given above.

The invention claimed is:

1. Osteosynthesis device comprising:
a plurality of vertebral implants, each implant comprising an attachment structure for a spinal support element and at least one of the implants comprising a universal joint between a screw head of the implant and a clamping support head of the implant, and a clamping support that is mobile with respect to the rest of the implant; and
an elongated spinal support element comprising
at least one longitudinally elongated opening on at least a first end of the elongated spinal support element, the at least one longitudinally elongated opening being configured for insertion in the attachment structure of a first one of the implants with the attachment structure of the first one of the implants assembled loosely, and
having a part with a substantially constant width configured to slide longitudinally in the loosely assembled attachment structure of the first one of the implants after being inserted therein,
the elongated spinal support element being configured
to be assembled at the first end of the elongated spinal support element on the first one of the implants,
to slide in relation to the attachment structure of the first one of the implants so that a second end of the elongated spinal support element can be inserted in the attachment structure of a second one of the implants with the attachment structure of the second one of the implants assembled loosely, and
to slide in relation the loosely assembled attachment structures of each of the first and second one of the implants to bring the elongated spinal support element into configuration for fixation by the attachment structures to each of the first and second one of the implants.

2. Osteosynthesis device according to claim 1 further comprising a screw head housing receiving the clamping support head, having a dimension that is sufficient to allow clearance and retention of the clamping support along a specified angle between an axis of the clamping support and an axis of the implant.

3. Osteosynthesis device according to claim 1 in which the clamping support head has a star shaped cross-section with rounded ends along a plane perpendicular to a support axis.

4. Osteosynthesis device according to claim 1 in which the clamping support comprises a threading cooperating with a nut to retain the elongated spinal support element against the clamping support.

5. Osteosynthesis device according to claim 1 in which an end of the clamping support is adapted to receive a rotational drive tool for said implant.

6. Osteosynthesis device comprising:
a plurality of vertebral implants, each implant comprising an attachment structure for a spinal support element; and a plate support retained on the implant that is rotatable about the implant;
an elongated spinal support element comprising
at least one longitudinally elongated opening on at least a first end of the elongated spinal support element, the at least one longitudinally elongated opening being configured for insertion in the attachment structure of a first one of the implants with the attachment structure of the first one of the implants assembled loosely, and
having a part with a substantially constant width configured to slide longitudinally in the loosely assembled attachment structure of the first one of the implants after being inserted therein,
the elongated spinal support element being configured
to be assembled at the first end of the elongated spinal support element on the first one of the implants,
to slide in relation to the attachment structure of the first one of the implants so that a second end of the elongated spinal support element can be inserted in the attachment structure of a second one of the implants with the attachment structure of the second one of the implants assembled loosely, and
to slide in relation the loosely assembled attachment structures of each of the first and second one of the implants to bring the elongated spinal support element into configuration for fixation between the attachment structure and the plate support of each of the first and second one of the implants.

7. Osteosynthesis device according to claim 6 in which the elongated spinal support element comprises two parts joined together by a joining part that is located in an inner part of the elongated spinal support element at a distance from the first and second ends of said elongated spinal support element sufficient to enable the attachment of the elongated spinal support element onto the first and second implants with the first and second implants disposed on opposite sides of the joining part.

8. Osteosynthesis device according to claim 7 in which the joining part is located in a position offset with respect to the center of the length of the elongated spinal support element.

9. Osteosynthesis device according to claim 6 in which the elongated spinal support element has peripheral edges that form an "H" or "h" shape.

10. Osteosynthesis device according to claim 6 in which the part of the at least one longitudinally elongated opening with a substantially constant width is located at a first region, and the at least one longitudinally elongated opening has a second region having a width larger than the width in the first region, the width in the second region sufficient to clear a clamp of the attachment structure of the first implant.

11. Osteosynthesis device according to claim 6 in which the attachment structure of at least one of the implants is configured to hold the elongated spinal support element while allowing said implant to rotate about its screwing axis with said attachment structure loosely assembled.

12. Osteosynthesis device according to claim 6 in which at least one of the implants has an elongated shape around an implant axis and comprises
a first bone anchoring threaded end;
a second end having an elongated part; and
a clamp along the elongated part of the second end for clamping the elongated spinal support element against the plate support.

13. Osteosynthesis device according to claim 6 in which the elongated spinal support element is configured to at least partially surround at least one of the implants and to rest on a surface of the plate support, the plate support having a concave surface in the form of a spherical portion configured to be supported on a head of said implant.

14. Osteosynthesis device according to claim 6 in which the elongated spinal support element is configured to at least partially surround at least one of the implants and to rest on a surface of the plate support, the plate support configured to be supported on a shoulder of said implant.

15. Osteosynthesis device according to claim 6 in which at least one of the implants comprises a clamping support having a first elongated end along a support axis and a second end having a clamping support head, the clamping support head having a non-circular cross-section along a plane perpendicular to the support axis and having at least one concave part and at least one dimension that is greater than at least one cross-section of the first elongated end of the clamping support; the clamping support head having a section that is substantially circular in cross section along a plane including the support axis, and being disposed in a screw head housing comprising at least one projecting part cooperating with the concave part of the clamping support head to prevent rotation of the clamping support around the support axis.

16. Osteosynthesis device according to claim 15 in which an inner surface of the screw head housing has a shape that is substantially complementary to the outer surface of the clamping support head.

17. Osteosynthesis device according to the claim 6 wherein at least one of the implants has a first bone anchorage end that has a longitudinal bore concentric to an outer surface, the bore communicating with space outside the outer surface through at least one bone fusion opening disposed in a wall between the longitudinal bore and the outer surface, the bone fusion opening being configured to allowing fusion between bone substance located inside the longitudinal bore and bone substance outside of the outer surface.

18. Osteosynthesis device according to claim 17 in which the first bone anchorage end has two threadings that are adapted to wind in the same direction along said implant, with one threadings being disposed on the outer surface and the other threading being disposed on the inner surface of the longitudinal bore.

19. Osteosynthesis device according to claim 6 further comprising at least one bone fusion opening in at least one of the implants comprising a longitudinal oblong hole.

20. Osteosynthesis device according to claim 6 in which the elongated spinal support element comprises one or more bars.

21. Osteosynthesis device according to claim 6 in which the elongated spinal support element comprises a plate.

22. Osteosynthesis device according to claim 6 in which the attachment structure of at least one of the implants is configured to hold the elongated spinal support element while allowing clearance of the elongated spinal support element with respect to the implant with said attachment structure loosely assembled.

23. A method for preassembling an osteosynthesis device comprising:
providing a device according to claim 6;
assembling a elongated spinal support element on a plate support of an implant; and
assembling an attachment structure on said implant.

24. Osteosynthesis device according to claim 6, in which at least one of the implants further comprises an anchor along a first portion of the implant and a clamping support along a second portion of the implant, the clamping support comprising a clamping support head disposed toward the anchor.

25. Osteosynthesis device according to claim 24 further comprising a screw head housing receiving the clamping support head, having a dimension that is sufficient to allow clearance and retention of the clamping support along a specified angle between an axis of the clamping support and an axis of the implant.

26. Osteosynthesis device according to claim 24 in which the clamping support head has a star shaped cross-section with rounded ends along a plane perpendicular to a support axis.

27. Osteosynthesis device according to claim 24 in which the clamping support comprises a threading cooperating with a nut to retain the elongated spinal support element against the clamping support.

28. Osteosynthesis device according to claim 24 in which an end of the clamping support is adapted to receive a rotational drive tool for said implant.

* * * * *